United States Patent
Tanaka et al.

(10) Patent No.: US 6,590,054 B2
(45) Date of Patent: Jul. 8, 2003

(54) ANTITHROMBOTIC SURFACE TREATING AGENT AND MEDICAL APPARATUS

(75) Inventors: Masaru Tanaka, Hokkaido (JP); Shoji Ochiai, Kanagawa (JP); Norifumi Tokunaga, Kanagawa (JP); Yukiko Irie, Fukuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/962,591

(22) Filed: Sep. 26, 2001

(65) Prior Publication Data

US 2002/0064558 A1 May 30, 2002

(30) Foreign Application Priority Data

Sep. 29, 2000 (JP) ........................................ 2000-299145

(51) Int. Cl.$^7$ ............................................... C08F 220/10
(52) U.S. Cl. ................... 526/328.5; 526/259; 526/265; 526/303.1; 526/307; 526/320
(58) Field of Search ................. 526/259, 265, 526/303.1, 307, 320, 328.5

(56) References Cited

U.S. PATENT DOCUMENTS

| | | | |
|---|---|---|---|
| 4,936,998 A | | 6/1990 | Nishimura et al. |
| 5,057,560 A | * | 10/1991 | Mueller ........................ 524/22 |
| 5,270,046 A | | 12/1993 | Sakamoto et al. |

FOREIGN PATENT DOCUMENTS

| EP | 0 859 403 A1 | 2/1998 |
|---|---|---|
| JP | 54-139660 * | 10/1979 |
| JP | 60-119955 | 6/1985 |
| JP | 60-119956 | 6/1985 |
| JP | 60-119957 | 6/1985 |
| JP | 61-163163 A | 7/1986 |
| JP | 4-152952 A | 5/1992 |
| JP | 4-152952 | 5/1992 |
| JP | 5-262656 A | 10/1993 |
| JP | 5-262656 | 10/1993 |
| WO | WO00/39176 | 7/2000 |

OTHER PUBLICATIONS

Andrade et al, "Surfaces and Blood Compatibility", *Trans Am Soc Artif. Intern. Organs*, (1987), pp. 75–84, vol. XXXIII.
Polymers and Remedy, Mita Publishing Association, (1989), pp. 71–73 and English translation, Japan.
Artificial Organs 16(2), (1987), p. 1045, Japan.
Artificial Organs 19(3), (1990), p. 1287 with English Abstract, Japan.
Tanaka M et al, "Blood compatible aspects of poly(2–methoxyethylacrylate) (PMEA)–relationship between protein adsorption and platelet adhesion on PMEA surface"; *Biomaterials*, Elsevier Science Publishers BV., Barking G.B., vol. 21, No. 14, Jul. 2000, pp. 1471–1481.
European Search Report issued in European Patent Document No. EP 01 12 3054, Feb. 11, 2002.

* cited by examiner

*Primary Examiner*—Helen L. Pezzuto

(57) ABSTRACT

A copolymer comprising a monomer of formula (1) below and a monomer having a basic functional group copolymerizable with the monomer as monomer components, wherein molar ratio of the monomer of formula (1) to the monomer having a basic functional group is 85/15 to 99.9/0.1 and wherein the copolymer has a number based mean molecular weight of 5,000 to 500,000. The copolymer is excellent in antithrombotic activity and further in biocompatibility and can be used as a medial material having high hydrophilicity. It also can serve as an antithrombotic surface treating agent.

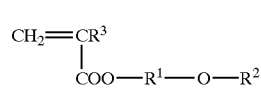

(1)

(wherein $R^1$ is an alkylene group having 1 to 4 carbon atoms, $R^2$ is an alkyl group having 1 to 4 carbon atoms, and $R^3$ represents hydrogen or a methyl group).

5 Claims, No Drawings

ANTITHROMBOTIC SURFACE TREATING AGENT AND MEDICAL APPARATUS

BACKGROUND OF THE INVENTION

1. Field of the Invention

The present invention relates to a copolymer that can be used as an antithrombotic surface treating agent and to an antithrombotic surface treating agent comprising such a copolymer. Also, the present invention relates to a medical apparatus and tool the surface of which is treated with the antithrombotic surface treating agent described above and to a method for producing such a medical apparatus or tool.

2. Description of the Related Art

Recently, studies on medical materials utilizing various polymer materials has been in progress and their application to blood filters, membranes for dialyzer, membranes for blood plasma separator, catheters, membranes for oxygenator, artificial blood vessels, membranes for preventing accretion, artificial skin or the like is expected. In this case, synthetic materials that are foreign materials to organisms are used in contact with tissues or blood in the organism so that the medical material must have biocompatibility.

Where a medial material is used as a material to be contacted with blood, the following three elements are important items of its biocompatibility: (a) inhibition of the blood coagulation system, (b) inhibition of the adhesion and activation of platelets, and (c) inhibition of activation of the complement system.

In particular, where it is used as a material to be contacted with blood only for a relatively short time, such as a medical material for extracorporeal circulation (for example, dialyzer, membrane of blood plasma separator, etc.), generally an anticoagulating agent such as heparin or sodium citrate is simultaneously used. Accordingly, the inhibition of activation of platelets and complement system as in (b) and (c) described above are important problems.

Regarding (b) the inhibition of the adhesion and activation of platelets above, it has been reported that a surface with micro phase separation or a hydrophilic surface, in particular a gelled surface having bonded thereon a water-soluble polymer is superior but a hydrophobic surface such as a surface of polypropylene is inferior (see, for example, Trans. Am. Soc. Artif. Intern. Organs, Vol. XXXIII, p. 75–84 (1987) and Polymers and Remedy, Mita Publishing Association, p. 73 (1989)).

Although the surface having a micro phase separation structure can exhibit good blood compatibility by controlling it to a suitable phase separation state, the conditions under which such a phase separation state can be made are limited and the material finds a limited application. The gelled surface having bonded thereon a water-soluble polymer can inhibit the adhesion of platelets. However, the platelets activated on the surface of the material and fine thrombi are returned into the body, which frequently causes the problem of extraordinary variation of blood cells (platelets).

Tsuruta et al. have proposed a polymer having a basic nitrogen containing functional group and a nitrogen content of 0.05 to 3.5% by weight as a surface to which platelets hardly adhere (Japanese Patent Application Laid-open Nos. 60-119955, 60-119956, and 60-119957). However, the polymer is based on HEMA (2-hydroxyethyl methacrylate) so that a problem arises that the activation of complement system takes place.

On the other hand, regarding (c) activation of the complement system, it is known that the surface of material having a hydroxyl group, such as cellulose or ethylene-vinyl alcohol copolymer, shows a high activity but a hydrophobic surface such as the surface of polypropylene shows a weak activity (see, for example, *Artificial Organs* 16(2), p. 1045–1050 (1987)).

Therefore, use of materials based on cellulose and vinyl alcohol, respectively in for example membranes for artificial organs causes the problem of activation of the complement system. On the contrary, use of hydrophobic surfaces such as the surface of polyethylene causes the problem of adhesion and activation of platelets.

Furthermore, where the medical material is used as a material to be contacted with blood for a relatively long time as in the case of an artificial blood vessel, it must be a material having affinity for the tissues (cells) in an organism in addition to the above 3 items so that neoplastic tunica intima formation and neogenesis and regeneration of tissues in the organism can take place suitably. The material for an artificial blood vessel includes, for example, ultra fine polyester fiber (Artificial Organs 19(3), p. 1287–1291 (1990)). The ultra fine polyester fiber is one of medical materials that utilize recognition of foreign matter by the organism, cure of wounds by biophylaxis, and self-to-self tissue regeneration, and is currently used mainly as an artificial blood vessel.

However, a prolonged application of the artificial blood vessel to microvessels causes the problem of their occlusion.

Moreover, for medial materials that contact tissues or fluid in the organism as well as blood, for example, membrane for preventing accretion and implanting material, which are implanted in the organism for a long period of time, or wound covering material used in contact with wounded portion (site where the skin is peeled and damaged to expose the tissue in the organism), a surface that is recognized by the organism as a foreign matter in few occasions and is readily peeled off from the organism (no accreting surface) is necessary.

However, in the case of silicone, polyurethane and polytetrafluoroethylene used as the above-described material, no satisfactory properties have been obtained yet since the tissue in the organism coalesce with the surface of the material or the recognition of it as a foreign matter by the organism is too intense.

Therefore, no polymer surface that satisfies simultaneously the biocompatibilities required for medical materials used in contact with the tissues in the organism or blood, such as inhibition of adhesion and activation of platelets, inhibition of activation of complement system and affinity for the tissues in the organism, has been obtained yet.

On the contrary, the present inventors have found that specified alkoxyalkyl (meth)acrylate polymer is excellent in antithrombosis and further in biocompatibility and proposed as a medical material (Japanese Patent Application Laid-open No. Hei 4-152952 (Japanese Patent No. 2806510) and Japanese Patent Application Laid-open No. Hei 5-262656).

However, the surface treated with these polymers is hydrophobic so that its application is limited and cannot be used for a variety of uses.

SUMMARY OF THE INVENTION

An object of the present invention is to provide a copolymer that is superior in antithrombotic property and further biocompatibility to the conventional medical materials and can be used as a medical material having high hydrophilicity.

Another object of the present invention is to provide a surface treating agent comprising such a copolymer.

Still another object of the present invention is to provide a medical apparatus having a surface treated with such an antithrombotic surface treating agent.

Yet another object of the present invention is to provide a method for producing such a medical apparatus.

The present inventors have made extensive studies with a view to solving the above problems and as a result they have found that a copolymer comprising a specified alkoxyalkyl (meth)acrylate and a monomer having a basic functional group copolymerizable with the specified monomer as monomer components and having a specified molar ratio of one to the other has antithrombotic property equivalent to or higher than and hydrophilicity higher than the conventional alkoxyalkyl (meth)acrylate homopolymer or the like. The present invention is based on this discovery.

That is, in accordance with a first embodiment of the present invention, there is provided a copolymer comprising a monomer of formula (1) below and a monomer having a basic functional group copolymerizable with the monomer as monomer components, wherein molar ratio of the monomer of formula (1) to the monomer having a basic functional group is 85/15 to 99.9/0.1 and wherein the copolymer has a number based mean molecular weight of 5,000 to 500,000.

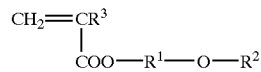
(1)

(wherein $R^1$ is an alkylene group having 1 to 4 carbon atoms, $R^2$ is an alkyl group having 1 to 4 carbon atoms, and $R^3$ represents hydrogen or a methyl group).

It is preferred that the monomer of formula (1) is 2-methoxyethyl (meth)acrylate.

In one of preferred modes, the monomer having a basic functional group comprises at least one monomer selected from the group consisting of monomers of formulae (2), (3), (4) and (5), respectively.

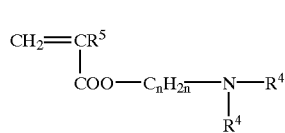
(2)

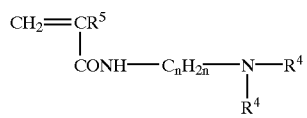
(3)

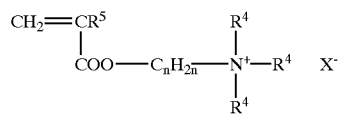
(4)

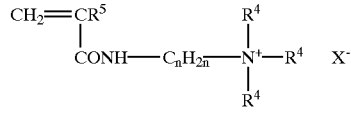
(5)

(wherein ($R^4$)s independently represent hydrogen or an alkyl group having 1 to 4 carbon atoms, ($R^5$)s independently represent hydrogen or a methyl group, n is an integer of 1 to 4, and ($X^-$)s independently represent an anion derived from halogen, sulfonic acid or sulfuric acid)

It is preferred that the monomer of formula (2) is at least one monomer selected from the group consisting of N,N-dimethylaminoethyl (meth)acrylate, N,N-dimethylaminopropyl (meth)acrylate, and N,N-diethylaminoethyl (meth)acrylate.

The monomer of formula (3) is preferably at least one monomer selected from N,N-dimethylaminopropylmethacrylamide and N,N-dimethylaminopropylacrylamide.

In one of preferred modes, the monomer having a basic functional group is at least one monomer selected from the group consisting of aminostyrene, N,N-dimethylaminostyrene, N,N-diethylaminostyrene, vinylpyridine, N-methyl-N-vinylpyridine, N-ethyl-N-vinylpyridine, vinylquinoline, ethyleneimine, propyleneimine, N-aminoethylethyleneimine, vinylimidazole, vinylpyrazoline, and vinylpyrazine.

In accordance with a second embodiment of the present invention, there is provided an antithrombotic surface treating agent, comprising the copolymer described above.

In accordance with a third embodiment of the present invention, there is provided a medical apparatus having a surface treated with the antithrombotic surface treating agent described above.

Preferably, the surface of the medical apparatus is made of polyurethane or polyester.

As the medical apparatus, a blood filter is one of preferred modes.

In accordance with a fourth embodiment of the present invention, there is provided a method for producing a medical apparatus, comprising the steps of: coating the antithrombotic surface treating agent described above on a surface of a medical apparatus, and heat-drying the agent.

The copolymer of the present invention is excellent in antithrombotic property and further in biocompatibility and can be used as a medical material having a high hydrophilicity.

The antithrombotic surface treating agent of the present invention comprising the copolymer of the invention can be advantageously used for the surface treatment of a medical apparatus such as a blood circuit or a membrane for an artificial organ.

The medical apparatus of the present invention has a surface treated with the antithrombotic agent of the invention so that it is excellent in antithrombotic property and further in biocompatibility.

The blood filter of the present invention comprises a filter whose surface is treated with the antithrombotic surface treating agent of the invention, so that it is excellent in antithrombotic property and can recover platelets efficiently.

The method for producing a medical apparatus according to the present invention can increase the adhesion between the filter and the copolymer of the present invention to fix the copolymer to the filter more firmly.

DETAILED DESCRIPTION OF THE INVENTION

The copolymer in accordance with the first embodiment of the present invention comprises as monomer components a monomer of the formula (1) above (hereinafter, also referred to as "alkoxyalkyl (meth)acrylate") and a monomer having a basic functional group copolymerizable with the monomer of the formula (1) above. Here, "(meth)acrylate" stands for acrylate and methacrylate.

In the formula (1) above, $R^1$ is an alkylene group having 1 to 4 carbon atoms, preferably 1 to 3 carbon atoms, and more preferably 1 or 2 carbon atoms, $R^2$ is an alkyl group having 1 to 4 carbon atoms, preferably 1 to 3 carbon atoms, and more preferably 1 or 2 carbon atoms, and $R^3$ represents hydrogen or a methyl group.

The alkoxyalkyl (meth)acrylate includes, for example, methoxymethyl (meth)acrylate, methoxyethyl (meth) acrylate, methoxypropyl (meth)acrylate, methoxybutyl (meth)acrylate, ethoxymethyl (meth)acrylate, ethoxyethyl (meth)acrylate, ethoxypropyl (meth)acrylate, ethoxybutyl (meth)acrylate, propoxymethyl (meth)acrylate, propoxyethyl (meth)acrylate, propoxypropyl (meth)acrylate, propoxybutyl (meth)acrylate, and the like. These monomers may be used alone or two or more thereof may be used in combination.

Among the above monomers, methoxyalkyl (meth) acrylates are preferred from the viewpoints of economy and ease of manipulation. In particular, 2-methoxyethyl (meth) acrylate is preferred.

The monomer having a basic functional group described above is not particularly limited as far as it can copolymerize with the alkoxyalkyl (meth)acrylates described above.

Examples of the basic functional group include primary amino groups, secondary amino groups, tertiary amino groups, quaternary ammonium salts, a pyridyl group, an aziridine group, and an imidazolyl group.

In the present invention, according to one of preferred modes, the comonomer having the basic functional group described above (monomer that can copolymerize with the alkoxyalkyl (meth)acrylate) comprises at least one monomer selected from the group consisting of the monomers of the formulae (2), (3), (4) and (5) above.

In the formulae (2) to (5) above, $(R^4)$s independently represent hydrogen or an alkyl group having 1 to 4 carbon atoms, preferably hydrogen or an alkyl group having 1 or 2 carbon atoms, and more preferably hydrogen or a methyl group, $(R^5)$s independently represent hydrogen or a methyl group, n is an integer of 1 to 4, and $(X^-)$s independently represent an anion derived from halogen, sulfonic acid or sulfuric acid. The anion derived from sulfuric acid includes hydrogen sulfate ion and sulfate ion.

The monomer of the formula (2) above includes aminoalkyl (meth)acrylates. Specific examples thereof include, for example, aminomethyl (meth)acrylate, aminoethyl (meth)acrylate, aminoisopropyl (meth)acrylate, amino-n-butyl (meth)acrylate, N-methylaminoethyl (meth)acrylate, N-ethylaminoisobutyl (meth)acrylate, N-isopropylaminomethyl (meth)acrylate, N-isopropylaminoethyl (meth)acrylate, N-n-butylaminoethyl (meth)acrylate, N-t-butylaminoethyl (meth)acrylate, N,N-dimethylaminomethyl (meth)acrylate, N,N-dimethylaminoethyl (meth)acrylate, N,N-dimethylaminopropyl (meth)acrylate, N,N-dimethylaminobutyl (meth)acrylate, N-methyl-N-ethylaminoethyl (meth)acrylate, N-methyl-N-butylaminoethyl (meth)acrylate, N,N-diethylaminoethyl (meth)acrylate, N,N-diethylaminopropyl (meth)acrylate, N,N-dipropylaminoethyl (meth)acrylate, N,N-dipropylaminopropyl (meth)acrylate, and N,N-diaminobutylpropyl (meth)acrylate.

The monomer of the formula (3) above includes aminoalkyl (meth)acrylamides. Specific examples thereof include, for example, aminomethyl (meth)acrylamide, aminoethyl (meth)acrylamide, aminoisopropyl (meth) acrylamide, amino-n-butyl (meth)acrylamide, N-methylaminoethyl (meth)acrylamide, N-ethylaminoisobutyl (meth)acrylamide, N-isopropylaminomethyl (meth)acrylamide, N-isopropylaminoethyl (meth)acrylamide, N-n-butylaminoethyl (meth)acrylamide, N-t-butylaminoethyl (meth)acrylamide, N,N-dimethylaminomethyl (meth) acrylamide, N,N-dimethylaminoethyl (meth)acrylamide, N,N-dimethylaminopropyl (meth)acrylamide N,N-dimethylaminobutyl (meth)acrylamide, N-methyl-N-ethylaminoethyl (meth)acrylamide, N-methyl-N-butylaminoethyl (meth)acrylamide, N,N-diethylaminoethyl (meth)acrylamide, N,N-diethylaminopropyl (meth) acrylamide, N,N-dipropylaminoethyl (meth)acrylamide, N,N-dipropylaminopropyl (meth)acrylamide, N,N-diaminobutylpropyl (meth)acrylamide and the like.

The monomers of the formulae (4) and (5) above are each derivatives obtained by treating the monomers of the formulae (2) and (3) above, respectively, with an alkyl halide, an alkyl sulfate or the like to convert them into quaternary ammonium salts.

In the present invention, according to one of preferred modes, the comonomer having a basic functional group comprises at least one monomer selected from the group consisting of aminostyrene, N,N-dimethylaminostyrene, N,N-diethylaminostyrene, vinylpyridine, N-methyl-N-vinylpyridine, N-ethyl-N-vinylpyridine, vinylquinoline, ethyleneimine, propyleneimine, N-aminoethylethyleneimine, vinylimidazole, vinylpyrazoline, and vinylpyrazine.

According to one of preferred modes, the comonomer having a basic functional group may comprise at least one derivative obtained by treating these monomers with an alkyl halide, an alkyl sulfate or the like to convert them into quaternary ammonium salts thereof.

The comonomers having a basic functional group may be used alone or two or more of them may be used in combination.

Particularly preferred comonomers among those described above are N,N-dialkylaminopropyl (meth) acrylamides corresponding to the formula (3) in which n is 3, which are easy to synthesize on an industrial scale and inexpensive, with N,N-dimethylaminopropyl methacrylamide and/or N,N-dimethylaminopropyl acrylamide being particularly preferred.

Also, the monomers of the formula (2) above in which n is 2 or 3 are preferred, in particular, at least one selected from the group consisting of N,N-dimethylaminoethyl (meth)acrylate, N,N-dimethylaminopropyl (meth)acrylate and N,N-diethylaminoethyl (meth)acrylate is preferred.

The copolymer of the present invention comprising as monomer components the monomer of the formula (1) above and the monomer having a basic functional group above is characterized in that the molar ratio of the monomer of the formula (1) above to the monomer having a basic functional group is 85/15 to 99.9/0.1.

By setting the molar ratio of the monomer of the formula (1) above to the monomer having a basic functional group within the above range, the copolymer of the present invention when used as a surface treating agent can have antithrombotic property equivalent or superior to and hydrophilicity superior to the case where the homopolymer of the monomer of the formula (1) above is used.

The molar ratio of the monomer of the formula (1) above to the monomer having a basic functional group is preferably 90/10 to 99/1 and more preferably 95/5 to 98/2.

The copolymer of the present invention has a number based average molecular weight of preferably 5,000 to 500,000 and more preferably 50,000 to 200,000. When the number based average molecular weight is in the above range, the elution thereof into blood or its cytotoxicity can be decreased.

The copolymer of the present invention may be any one of random copolymer, block copolymer and graft copolymer. The copolymerization reaction for producing the copolymer of the present invention is not particularly limited and any known method such as radical polymerization, ion polymerization, photo polymerization, polymerization using a macromer or the like may be employed.

The copolymer of the present invention as described above is insoluble in water and can be used as a surface treating agent.

In accordance with the second embodiment, the present invention relates to an antithrombotic surface treating agent comprising the copolymer described above.

The antithrombotic surface treating agent of the invention may comprise any one of the copolymers of the present invention or two or more of them in admixture.

The antithrombotic surface treating agent of the present invention is excellent in antithrombotic property and further in biocompatibility so that it can be advantageously used in surface treatment of medical apparatus and membranes for use in artificial organs.

In particular, the antithrombotic surface treating agent of the present invention is superior in hydrophilicity to the homopolymer of the monomer of the formula (1) above and hence it can be used in a variety of applications. For example, it can be used for various base materials that are subjected to be surface treatment. Examples of hydrophilic base material include polyurethane, cellulose, polyamide, poly(meth)acrylate, natural polymers (for example, cotton, hemp, etc.), and the like and examples of hydrophobic base material include polypropylene, polycarbonate, polyester, polyvinyl chloride, polysulfone, and polyacrylonitrile, and the like. These materials may be selected suitably depending on the purpose. Among them, preferred base materials include polyurethane, polypropylene, polycarbonate, polyester, and polyvinyl chloride.

The surface treated with the antithrombotic surface treating agent of the present invention is hydrophilic. Therefore, it has excellent wettability to the body fluid such as blood. For example, it is advantageous in that when the surface of blood circuit or membrane for artificial organ is treated to have such a surface, foams hardly attach to the surface.

The surface treated with the antithrombotic surface treating agent of the present invention has a contact angle of water of preferably 36 to 60 degrees, more preferably 38 to 50 degrees.

In accordance with the third embodiment, the present invention relates to a medical apparatus having a surface treated with the antithrombotic surface treating agent of the present invention. The medical apparatus of the present invention is treated with the antithrombotic surface treated agent of the present invention over at least a portion of the surface, preferably over its entire surface that contacts blood or the like.

The medical apparatus of the present invention is the one of which excellent antithrombotic property is required according to one of preferred modes. Examples of such a medical apparatus include a blood filter, a blood storage bag, a blood circuit, an indwelling needle, a catheter, a guide wire, a stent, an oxygenator, a dialyzer, a coalescence preventing material, a wound covering material, an adhesive for tissues, and a repairing material for tissue regeneration. In particular, according to a preferred mode, the medical apparatus of the present invention has an extracorporeal circulation circuit having a blood contact portion therein.

The medical apparatus of the present invention preferably has a polyurethane or polyester surface treated with the antithrombotic surface treating agent of the present invention. when the surface is constituted by polyurethane or polyester, the layer treated with the antithrombotic surface treating agent of the present invention (the film of the copolymer of the present invention) hardly is peeled off.

Among those described above as preferred medical apparatuses of the present invention, the blood filter is one of the particularly preferred modes.

The blood filter of the present invention comprises a filter material in which at least a portion, preferably the whole of the surface thereof is treated with the antithrombotic surface treating agent of the present invention. Here, the surface of a filter means the both surfaces of the filter on which blood contacts and surface portion of the pores in the filter.

The shape of the blood filter of the present invention is not particularly limited. For example, it may be in the form of a porous material, a thread, a nonwoven fabric, particles, a film, a sheet, a tube, a hollow fiber, or powder. Among them, a porous material and a nonwoven fabric are preferred.

In the case of a porous material, it has a mean flow pore diameter of preferably 1 to 20 $\mu$m measured using a perm porosimeter. If the mean flow pore diameter is below 1 $\mu$m, the filter tends to be clogged while if it is above 20 $\mu$m, the removal ratio of leukocyte described below may sometimes decrease to 50% or less.

The material of the blood filter of the present invention includes, for example, natural polymers such as cotton and hemp; synthetic polymers such as nylon, polyester, polyacrylonitrile, polyolefin, halogenated polyolefin, polyethylene terephthalate, polyurethane, polyamide, polysulfone, polyethersulfone, poly(meth)acrylate, ethylene-polyvinyl alcohol copolymer and butadiene-acrylonitrile copolymer; and mixtures of these.

In particular, when the blood filter of the present invention is made in the form of a porous material, it is preferred that polyurethane be used and when it is made in the form of a nonwoven fabric, use of polyethylene terephthalate is preferred.

The blood filter of the present invention is a filter that is used for removing leukocytes from the liquid containing platelets and leukocytes and is used mainly in the preparation, treatment, etc., for blood products such as platelet preparation, with targeting whole blood, platelet concentrate (PC), platelet rich plasma (PRP), and the like.

The blood filter of the present invention can be used as a cell separation filter such as a filter for collecting hematopoietic stem cells.

The filter incorporated in the blood filter of the present invention includes, for example, sponge-like, porous, nonwoven fabrics comprising polyester fiber. The filter is treated with the antithrombotic surface treating agent of the present invention on its surface to bear the copolymer of the present invention on the surface thereof.

The method for having the copolymer of the present invention carried on the surface of the filter includes known methods such as a coating method; a method using graft polymerization with radiation, electron beam or ultraviolet rays; and a method using a chemical reaction with the functional group of a base material. Among them, the coating method is practically preferred since it is simple in production step.

The application method is not particularly limited, and any of a coating method, a spraying method, a dipping method and the like may be used.

For example, the application of the copolymer of the present invention by a dipping coating method may be practiced by a simple operation such as by dipping a filter in a coating solution comprising a suitable organic solvent such as alcohol, chloroform, acetone, tetrahydrofuran or dimethylformamide having dissolved therein the antithrombotic surface treating agent of the present invention, removing excessive solution, and then air-drying the filter.

It is preferred that the filter after coating be heated to dry it. This increases the adhesion between the filter and the copolymer of the present invention to thereby fix the copolymer to the filter more firmly.

The treating method described above is not limited to the case where the medical apparatus of the present invention is a blood filter but can be applied to all the medical apparatuses. That is, the present invention provides a method for producing a medical apparatus, comprising the steps of coating the antithrombotic surface treating agent of the present invention on a surface of a medical apparatus, and heat-drying the agent.

The blood filter of the present invention has a leukocyte removal ratio of preferably 99% or more and more preferably 99.5% or more.

The blood filter of the present invention can realize high bleeding out rate and high filtration rate because of excellent blood compatibility and wettability to blood of the copolymer of the present invention.

Also, the blood filter of the present invention can be readily controlled of its leukocyte adsorbability by suitably changing the composition and ratio of the comonomer having a basic functional group that constitutes the copolymer.

Further, the blood filter of the present invention exhibits high removal rate for leukocytes and shows less activation of blood components such as blood bradykinin increase, so that it will not decrease the quality of blood after the filtration.

Furthermore, the blood filter of the present invention exhibits high platelet recovery ratio and the blood after the filtration does not cause hemolysis so that it is excellent in long-term storage of blood.

EXAMPLES

Hereinafter, the present invention will be described in detail by examples. However, the present invention is not limited thereto. Examples 1 to 5 and Comparative Examples 1 to 4 relate to production of surface treating agents and Test Examples 1 to 4 relate to blood filtration performance and blood compatibility of surface treating agents.

1. Preparation of the Surface Treating Agents

Example 1

To 20 g of 2-methoxyethyl acrylate (MEA; produced by Osaka Organic Chemistry, hereinafter the same) and 1.3 g of N,N-dimethylaminopropylacrylamide (DMAPAAm; produced by Aldrich, hereinafter the same) was added azobisisobutyronitrile (radical polymerization initiator; produced by Tokyo Kasei, hereinafter the same) in an amount of 0.1% by weight based on the total weight of monomers and the mixture was allowed to polymerize in 80 g of 1,4-dioxane (produced by Kanto Chemical) at 80° C. for 10 hours. After completion of the polymerization, the reaction solution was dripped into n-hexane (produced by Kanto Chemical) to form precipitates and the product was isolated. The product was dissolved in acetone (produced by Kanto Chemical) and the resulting solution was dripped into n-hexane and thus purified twice. The purified product was dried under reduced pressure over a whole day to obtain surface treating agent 1.

The composition (molar ratio of monomer components) of the obtained polymer was determined by $^1$H-NMR. The molar ratio of monomers was MEA/DMAPAAm=95/5.

Example 2

The same procedures were repeated as in Example 1 except that 17.5 g of MEA and 2.5 g of DMAPAAm were used as the starting materials to obtain surface treating agent 2. The molar ratio of monomers was MEA/DMAPAAm=90/10.

Example 3

To 20 g of MEA and 0.48 g of N,N-dimethylaminoethyl methacrylate (DMAEMA; produced by Wako Pure Chemical Industry) was added azobisisobutyronitrile in an amount of 0.05% by weight based on the total weight of monomers and the mixture was allowed to polymerize in 80 g of dimethylformamide (DMF; produced by Kanto Chemical) at 75° C. for 10 hours. After completion of the polymerization, the reaction solution was dripped into n-hexane to form precipitates and the product was isolated. The product was dissolved in tetrahydrofuran (THF) and the resulting solution was dripped into n-hexane and thus purified twice. The purified product was dried under reduced pressure over a whole day to obtain surface treating agent 3. The molar ratio of monomers was MEA/DMAEMA=98/2.

Example 4

The same procedures were repeated as in Example 3 except that 20 g of MEA and 1.2 g of DMAEMA were used as the starting materials to obtain surface treating agent 4. The molar ratio of monomers was MEA/DMAEMA=95/5.

Example 5

The same procedures were repeated as in Example 3 except that 17.6 g of MEA and 2.4 g of DMAEMA were used as the starting materials to obtain surface treating agent 5. The molar ratio of monomers was MEA/DMAEMA=90/10.

Comparative Example 1

To 20 g of 2-hydroxyethyl methacrylate (HEMA; produced by Wako Pure Chemical Industry) and 1.2 g of DMAEMA was added azobisisobutyronitrile in an amount of 0.05% by weight based on the total weight of monomers and the mixture was allowed to polymerize in 80 g of ethanol (produced by Kanto Chemical) under the conditions of 70° C. for 8 hours to obtain surface treating agent 6. The molar ratio of monomers was HEMA/DMAEMA=95/5.

Comparative Example 2

Poly(N,N-dimethylaminopropylacrylamide (PDMAPAAm)), which is an amine homopolymer, was used as surface treating agent 7.

Comparative Example 3

The same procedures were repeated as in Example 3 except that 15 g of MEA and 14.3 g of DEAEMA were used as the starting materials to obtain surface treating agent 8. The molar ratio of monomers was MEA/DEAEMA=60/40.

Comparative Example 4

Poly(2-methoxyethyl acrylate) (PMEA), which is a homopolymer, was used as surface treating agent 9.

2. Evaluation of Performance of Various Surface Treating Agents

Test Example 1

The surface treating agents prepared in Examples 1 to 5 and Comparative Examples 1 to 4 were each dissolved in a mixed solution of water and methanol (water/methanol=1/1 (v/v)) to a concentration of 0.05% by weight, and each of the solutions was coated on a polyurethane (PU) porous material (E394 POTA, produced by Nippon Miractorane; mean pore diameter: 5 $\mu$m, porosity: 85%) and then washed by showering with warm water at 60° C. for 4 hours. After drying it, the resulting blood filter was punched to obtain disks of a size of 1.2 mm in thickness and 30 mm in diameter to thereby obtain the blood filters. These blood filters were assembled in a blood circuit and fresh human blood was filtered therethrough. Further, a PC porous material without treated by the surface treating agents was also subjected to the filtration of fresh human blood in the same manner.

Weights of blood before and after filtration, concentration of leucocytes, and concentration of platelets were calculated using automatic blood cell counter (Sysmex NE-6000, produced by Toa Medical Electronics) and platelet recovery ratio was obtained by the following equation. The leaked leukocyte number was determined by the Nageotte method.

Platelet recovery ratio (%)=((number of platelets after filtration)/(number of platelets before filtration))×100

The results obtained are shown in Table 1.

TABLE 1

| | Surface treating agent | Composition | Platelet recovery ratio (%) | Leaked leukocyte number (x10²/µL) |
|---|---|---|---|---|
| Example 1 | 1 | MEA/DMAPMAAm = 95/5 | 91.4 | 4.3 |
| Example 2 | 2 | MEA/DMAPMAAm = 90/10 | 90.5 | 6.0 |
| Example 3 | 3 | MEA/DMAEMA = 98/2 | 93.2 | 4.5 |
| Example 4 | 4 | MEA/DMAEMA = 95/5 | 92.4 | 8.9 |
| Example 5 | 5 | MEA/DMAEMA = 90/10 | 93.7 | 6.0 |
| Comparative Example 2 | 7 | PDMAPAAm | 7.4 | 0.8 |
| Comparative Example 3 | 8 | MEA/DMAEMA = 60/40 | 8.7 | 1.1 |
| Comparative Example 4 | 9 | PMEA | 92.9 | 53.7 |
| Comparative Example | No treatment | — | 89.7 | 45.1 |

From Table 1, it will be apparent that use of the surface treating agents 1 to 5 obtained in Examples 1 to 5 gave excellent platelet recovery ratio and excellent leukocyte removal ability.

On the other hand, non-treated PU porous material without any coating showed a high platelet recovery ratio as high as 89.7% but showed a large leaked leukocyte number as compared with the use of the surface treating agents of the present invention obtained in the examples.

When the amine homopolymer of Comparative Example 2 (surface treating agent 7) or the copolymer having an amine content of 40% by mole of Comparative Example 3 (surface treating agent 8) is used, the leaked leukocyte number is small but the platelet recovery ratio is as low as 10% or less so that selective removal of only leukocytes can not be practiced.

Furthermore, when the PMEA of Comparative Example 4 (surface treating agent 9) was used, the platelet recovery ratio was as high as 92.9% but the leaked leukocyte number was large.

From the above results, it can be seen that use of the surface treating agent of the present invention enables one to make a filter surface that can selectively remove leukocytes while maintaining platelet recovery ratio at high levels.

Test Example 2

The surface treating agent 1 of Example 1 and surface treating agent 6 of Comparative Example 1 were each dissolved in a mixed solution of THF and methanol (THF/methanol=5/1 (v/v)) to a concentration of 0.1% by weight, and a polyethylene terephthalate (PET) sheet (polyester film A8300, produced by Toyobo) was dipped in each of the solutions for 10 seconds and drawn out, followed by drying each sheet over a whole day to prepare samples.

The samples thus obtained were evaluated on in vitro blood compatibility.

Using an evaluation circuit having a surface area of 120 cm² (a circulation system having a blood passage: 270 $\mu$m, blood: 25 ml/module), 2 U/ml heparin-added fresh human blood was flown under the conditions of flow rate of 3.5 ml/minute, a spacer of 270 $\mu$m and share rate of 160/second for 60 minutes. As an index of complement activity, C3a after the blood circulation was measured and the ratio of C3a after blood circulation to C3a before blood circulation (pre-value) was obtained.

The results obtained are shown in Table 2.

TABLE 2

| | Surface treating agent | Composition | Complement activity (C3a) (Ratio to PET) |
|---|---|---|---|
| Example 1 | 1 | MEA/DMAPMAAm = 95/5 | <1/5 |
| Comparative Example 1 | 6 | HEMA/DMAEMA = 95/5 | >1 |

From Table 2, it can be seen that the surface treated with surface treating agent 1 of Example 1 showed a low complement activity in human blood circulation tests.

On the other hand, surface treating agent 6 of Comparative Example 1 showed considerable complement activity.

Test Example 3

The surface treating agents 1 to 9 of Examples 1 to 5 and Comparative Examples 1 to 4 were each dissolved in methanol to a concentration of 0.1% by weight, and a polyurethane (PU) sheet (E394 POTA, produced by Nippon Miractorane) was dipped in each of the solutions for 10 seconds and drawn out, followed by drying each sheet over a whole day to prepare samples.

The samples thus obtained were subjected to platelet adhesion tests as follows. Also, PU sheets without treatment with a surface treating agent were subjected to the platelet adhesion tests in the same manner.

First, a collected blood to which CPD liquid was added in a proportion of 7/50 relative to the amount of collected blood was centrifuged at 1200 rpm for 5 minutes to separate PRP (platelet rich plasma). After separating PRP, further centrifugation was performed at 3,000 rpm for 10 minutes to obtain PPP (platelet poor plasma). Then, PRP was diluted with PPP to adjust the number of platelet to $1\times10^5$ cell/$\mu$L. 0.2 mL of diluted PRP was gently dripped on each sample. After leaving them to stand at room temperature for 30 minutes, the samples were rinsed twice with the dilution liquid and fixed in a 1% by weight PBS solution of glutaraldehyde at 4° C. over 1 day. They were subjected to ion sputtering and observed on SEM (JEOL JSM-840) with taking photographs (1,000×, 5 views). This procedure was repeated 3 times and a mean value was calculated for each sample.

In addition, platelet adhesion tests were performed using a PET sheet (Polyester film A8300) instead of the PU sheet.

The results obtained are shown in Table 3 (in the case where the PU sheet was used) and in Table 4 (in the case where the PET sheet was used). The platelet that retained round shape was named "Type I", the platelet that had some pseudopods was named "Type II", and the platelet that extended lost the original shape was named "Type III".

As will be apparent from Tables 3 and 4, as a result of platelet adhesion tests, the surfaces treated with the surface treating agents of the present invention obtained in Examples 1 to 5 inhibited platelet adhesion better than the surfaces treated with the surface treating agents of Comparative Examples 1 to 4 and the non-treated surfaces.

Paying attention to the morphology of the adhered platelet, the surfaces treated with the surface treating agents of Comparative Examples 1 to 4 and the non-treated surfaces contained platelets that had pseudopods whereas the surfaces treated with the surface treating agents of the Examples of the present invention contained platelets that retained round shape.

Test Example 4

In the same manner as in Test Example 1, the surface treating agents 1, 3, 4, 7, 8 and 9 of Examples 1, 3 and 4 and Comparative Examples 2 to 4 were each dissolved in a mixed solution of water and methanol and each of the obtained solutions was coated on a PU porous material (E394 POTA) to produce blood filters. The blood filters thus obtained were each incorporated in a blood circuit and fresh human blood was filtered therethrough. Similarly, fresh human blood was filtered through PU porous materials and polyethylene terephthalate (PET) porous materials that had no treatment with a surface treating agent.

TABLE 3

| Surface | | | Platelet Adhesion Number (cell/(8.5 × 10$^{-3}$ mm$^2$)) | | | |
|---|---|---|---|---|---|---|
| | treating agent | Composition | Type I | Type II | Type III | Sum |
| Example 1 | 1 | MEA/DMAPMAAm = 95/5 | 3.1 | 1.8 | 1.2 | 6.1 |
| Example 2 | 2 | MEA/DMAPMAAm = 90/10 | 5.1 | 2.3 | 2.0 | 9.4 |
| Example 3 | 3 | MEA/DMAEMA = 98/2 | 7.1 | 3.1 | 0.7 | 10.9 |
| Example 4 | 4 | MEA/DMAEMA = 95/5 | 4.1 | 2.1 | 1.9 | 8.1 |
| Example 5 | 5 | MEA/DMAEMA = 90/10 | 3.2 | 2.2 | 1.0 | 7.0 |
| Comparative Example 1 | 6 | HEMA/DMAEMA = 95/5 | 11.0 | 14.8 | 34.3 | 60.1 |
| Comparative Example 2 | 7 | PDMAPAAm | 8.6 | 19.8 | 325.2 | 353.6 |
| Comparative Example 3 | 8 | MEA/DMAEMA = 60/40 | 9.3 | 13.1 | 54.3 | 76.7 |
| Comparative Example 4 | 9 | PMEA | 10.2 | 3.4 | 0.1 | 13.7 |
| Comparative Example | No treatment | — | 10.7 | 11.7 | 28.7 | 51.1 |

TABLE 4

| Surface | | | Platelet Adhesion Number (cell/(8.5 × 10$^{-3}$ mm$^2$)) | | | |
|---|---|---|---|---|---|---|
| | treating agent | Composition | Type I | Type II | Type III | Sum |
| Example 1 | 1 | MEA/DMAPMAAm = 95/5 | 6.5 | 0.8 | 1.3 | 8.6 |
| Example 2 | 2 | MEA/DMAPMAAm = 90/10 | 8.9 | 3.2 | 0.9 | 13.0 |
| Example 3 | 3 | MEA/DMAEMA = 98/2 | 8.3 | 4.3 | 0.5 | 13.1 |
| Example 4 | 4 | MEA/DMAEMA = 95/5 | 3.5 | 3.2 | 2.1 | 8.8 |
| Example 5 | 5 | MEA/DMAEMA = 90/10 | 2.4 | 2.1 | 1.8 | 6.3 |
| Comparative Example 1 | 6 | HEMA/DMAEMA = 95/5 | 13.9 | 21.8 | 52.4 | 88.1 |
| Comparative Example 2 | 7 | PDMAPAAm | 3.2 | 17.5 | 356.7 | 377.4 |
| Comparative Example 3 | 8 | MEA/DMAEMA = 60/40 | 10.1 | 11.8 | 58.3 | 80.2 |
| Comparative Example 4 | 9 | PMEA | 9.8 | 6.1 | 0.8 | 16.7 |
| Comparative Example | No treatment | — | 0.9 | 8.9 | 492.1 | 501.9 |

AS an index of platelet activation, the value of β-TG after the blood filtration was measured and a ratio to the value of β-TG before the blood filtration (β-TG activation value) was calculated.

The results obtained are shown in Table 5.

TABLE 5

| | Surface treating agent | β-TG activation value |
|---|---|---|
| Example 1 | 1 | 0.58 |
| Example 3 | 3 | 0.73 |
| Example 4 | 4 | 0.65 |
| Comparative Example 2 | 7 | 17.59 |
| Comparative Example 3 | 8 | 1.28 |
| Comparative Example 4 | 9 | 1.06 |
| Comparative Example | (PU) | 1.35 |
| Comparative Example | (PET) | 6.89 |
| Blood before filtration | | 1.00 |

As will be apparent from Table 5, as a result of human blood circulation tests, the surfaces of the filters treated with the surface treating agents 1, 3 and 4 of the present invention obtained in Examples 1, 3 and 4 showed lesser activation of platelets than the non-treated surfaces and the surfaces of the filter treated with the surface treating agents 7 to 9 obtained in Comparative Examples 2 to 4.

Test Example 5

The surface treating agents 1 to 5 and 7 to 9 of Examples 1 to 5 and Comparative Examples 2 to 4 were each dissolved in a mixed solution of THF and methanol (THF/methanol= 5/1 (v/v)) to a concentration of 0.1% by weight, and a polyethylene terephthalate (PET) sheet (polyester film A8300, produced by Toyobo) was dipped in each of the solutions for 10 seconds and drawn out, followed by drying each sheet over a whole day to prepare samples.

The obtained samples were each measured for static contact angle of their surface. Measurement of static contact angle of the surface was performed using a contact angle meter (produced by Elma Optics). Non-treated PET sheet and PU sheet were also subjected to measurement of static contact angle of the surface.

The results obtained are shown in Table 6.

TABLE 6

| | Surface treating agent | Composition | Contact angle (°) |
|---|---|---|---|
| Example 1 | 1 | MEA/DMAPMAAm = 95/5 | 42 |
| Example 2 | 2 | MEA/DMAPMAAm = 190/10 | 38 |
| Example 3 | 3 | MEA/DMAEMA = 98/2 | 46 |
| Example 4 | 4 | MEA/DMAEMA = 95/5 | 44 |
| Example 5 | 5 | MEA/DMAEMA = 90/10 | 39 |
| Comparative Example 2 | 7 | PDMAPAAm | 29 |
| Comparative Example 3 | 8 | MEA/DMAEMA = 60/40 | 35 |
| Comparative Example 4 | 9 | PMEA | 52 |
| Comparative Example | No treatment (PU) | — | 68 |
| Comparative Example | No treatment (PET) | — | 79 |

As will be apparent from Table 6, the surfaces treated with the surface treating agents 1 to 5 of Examples 1 to 5 are higher in hydrophilicity than the non-treated surfaces and the surface treated with the surface treating agent 9 of Comparative Example 4. Therefore, the surfaces treated with the surface treating agents of the present invention have high wettability to blood and improved defoamability (difficulty in foam attachment). Accordingly, the surface treating agents of the present invention are useful as a surface treating agent for various medical apparatus such as a blood circuit, an artificial lung, a blood reservoir, and a catheter.

The surfaces treated with the surface treating agents 7 and 8 of Comparative Examples 2 and 3 are excellent in hydrophilicity but receives an intense influence of amine to have greater positive charge as compared with the surfaces treated with the surface treating agents of Examples, respectively, so that they show high non-specific adsorption of a blood cell component such as platelet and a plasma component.

Test Example 6

Samples were prepared in the same manner as in Test Example 1 except that a polyvinyl chloride base material or aluminum base material was used instead of the PU porous material and treated with each of the surface treating agents 1 to 5 of Examples 1 to 5, respectively, to prepare samples.

The samples obtained were observed on an X-ray optoelectronic spectrophotometer (JPS-90SX, produced by Nippon Denshi) to examine if chlorine atoms in the case of polyvinyl chloride base material or aluminum atoms in the case of aluminum base material are present on the surface of the base material.

As a result, no peak attributable to aluminum atom was observed in each of the polyvinyl chloride base materials. No peak attributable to aluminum atom was observed in each of the aluminum base material either. That is, it is confirmed that each of the base materials can be coated with the surface treating agent of each of the Examples 1 to 5.

What is claimed is:

1. An antithrombotic surface treating agent comprising a copolymer comprising a first monomer of formula (1) and a second monomer which is at least one monomer selected from the group consisting of monomers of formulae (2), (3), (4) and (5), as monomer components, wherein the molar ratio of the first monomer to the second monomer is 85/15 to 99.9/0.1, wherein the copolymer has a number based mean molecular weight of 5,000 to 500,000;

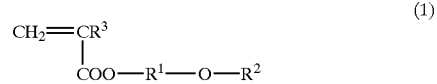

wherein $R^1$ is an alkylene group having 1 to 4 carbon atoms, $R^2$ is an alkyl group having 1 to 4 carbon atoms, and $R^3$ represents hydrogen or a methyl group,

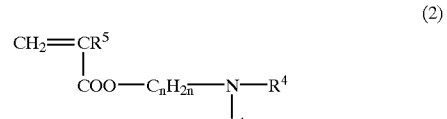

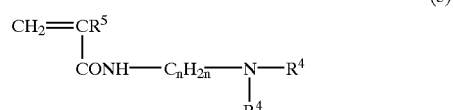

-continued

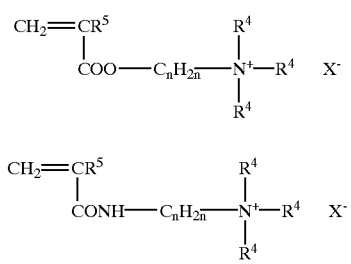

wherein each $R^4$ independently represents hydrogen or an alkyl group having 1 to 4 carbon atoms, $R^5$ independently represents hydrogen or a methyl group, n is an integer of 1 to 4, and X— independently represents an anion derived from halogen, sulfonic acid or sulfuric acid.

2. An antithrombotic surface treating agent according to claim 1, wherein the monomer of formula (1) is 2-methoxyethyl (meth)acrylate.

3. An antithrombotic surface treating agent according to claim 1, wherein the monomer of formula (2) is at least one monomer selected from the group consisting of N,N-dimethylaminoethyl (meth)acrylate, N,N-dimethylaminopropyl (meth)acrylate, and N,N-diethylaminoethyl (meth)acrylate.

4. An antithrombotic surface treating agent according to claim 1, wherein the monomer of formula (3) is at least one monomer selected from the group consisting of N,N-dimethylaminopropylmethacrylamide and N,N-dimethylaminopropylacrylamide.

5. A method of providing antithrombotic property and biocompatibility to a medical material comprising the step of:
   treating a surface of the medical material with an antithrombotic surface treating agent comprising a copolymer comprising a first monomer of formula (1) and a second monomer which is at least one monomer selected from the group consisting of monomers of formulae (2), (3), (4) and (5), respectively, as monomer components, wherein molar ratio of the first monomer to the second monomer is 85/15 to 99.9/0.1 and wherein the copolymer has a number based mean molecular weight of 5,000 to 500,000;

wherein $R^1$ is an alkylene group having 1 to 4 carbon atoms, $R^2$ is an alkyl group having 1 to 4 carbon atoms, and $R^3$ represents hydrogen or a methyl group,

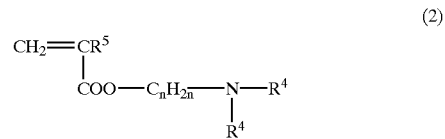

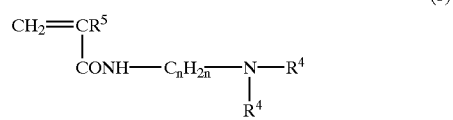

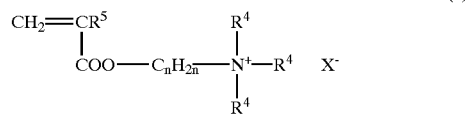

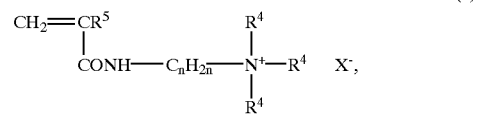

wherein each $R^4$ independently represents hydrogen or an alkyl group having 1 to 4 carbon atoms, $R^5$ independently represents hydrogen or a methyl group, n is an integer of 1 to 4, and X— independently represents an anion derived from halogen, sulfonic acid or sulfuric acid.

* * * * *